United States Patent
Yu et al.

(10) Patent No.: US 11,746,146 B2
(45) Date of Patent: Sep. 5, 2023

(54) ANTIBODY COMPOSITION SPECIFICALLY RECOGNIZING AN IMMUNOGENIC FRAGMENT PEPTIDE OF EN2 PROTEIN

(71) Applicant: SUNG KYUN BIOTECH CO., LTD., Suwon-si (KR)

(72) Inventors: Kyeong-Nam Yu, Suwon-si (KR); Eun-Yi Cho, Yongin-si (KR); Seung-Hee Chang, Anyang-si (KR); Seon-Hee Kim, Gwacheon-si (KR); Hyun-Suk Kim, Seoul (KR); Ki-Moon Park, Seongnam-si (KR)

(73) Assignee: SUNG KYUN BIOTECH CO., LTD., Suwon-si (KR)

( * ) Notice: Subject to any disclaimer, the term of this patent is extended or adjusted under 35 U.S.C. 154(b) by 0 days.

(21) Appl. No.: 17/553,779

(22) Filed: Dec. 16, 2021

(65) Prior Publication Data
US 2022/0106368 A1  Apr. 7, 2022

Related U.S. Application Data

(62) Division of application No. 16/488,238, filed as application No. PCT/KR2017/013631 on Nov. 28, 2017, now Pat. No. 11,498,945.

(30) Foreign Application Priority Data

Feb. 23, 2017 (KR) ........................ 10-2017-0024006

(51) Int. Cl.
| C07K 16/18 | (2006.01) |
| C07K 14/47 | (2006.01) |
| G01N 33/574 | (2006.01) |

(52) U.S. Cl.
CPC .............. *C07K 16/18* (2013.01); *C07K 14/47* (2013.01); *C07K 14/4702* (2013.01); *G01N 33/57434* (2013.01)

(58) Field of Classification Search
CPC ... C07K 14/47; C07K 16/18; G01N 33/57434
See application file for complete search history.

(56) References Cited

U.S. PATENT DOCUMENTS

| 8,460,882 B2 | 6/2013 | Pandha et al. |
| 8,722,643 B2 | 5/2014 | Donald |
| 9,429,575 B2 | 8/2016 | Ban et al. |
| 2012/0071347 A1 | 3/2012 | Donald |
| 2012/0177672 A1 | 7/2012 | Morgan et al. |

FOREIGN PATENT DOCUMENTS

| CN | 101675341 A | 3/2010 |
| EP | 2115472 B1 | 11/2013 |
| JP | 2012532621 A | 12/2012 |
| KR | 1020090111307 A | 10/2009 |
| KR | 1020160077788 A | 7/2016 |
| WO | 2008075056 A1 | 6/2008 |

OTHER PUBLICATIONS

Benjamini et al, 1991. Immunology: A Short Course, 2nd edition, p. 40 only.*
Ferrara et al (2015. mAbs. 7(1): 32-41).*
Database Geneseq:AAW93379. Jun. 8, 1999.
Database UniProt:G3SAI3. Nov. 16, 2011.
Database UniProt:S9WUW7. Oct. 16, 2013.
Morgan, R. et al., "Engrailed-2 (EN2): A Tumor Specific Urinary Biomarker for the Early Diagnosis of Prostate Cancer", Clinical Cancer Research, Mar. 1, 2011, vol. 17, No. 5, pp. 1090-1098.
NCBI. GenBank Accession No. NP_001418.2, "Homeobox Protein Engrailed-2 [*Homo sapiens*]", Oct. 6, 2016.
Chinese Office Action in the counterpart Chinese application No. 201780074265.8 dated Apr. 20, 2022.

* cited by examiner

*Primary Examiner* — Zachary C Howard
(74) *Attorney, Agent, or Firm* — Rabin & Berdo, P.C.

(57) ABSTRACT

The present invention relates to an immunogenic fragment peptide of an EN2 protein or an antibody composition specifically recognizing the same. In the present invention, EN2 protein can be quantified through a method of specifically recognizing the peptide. Also, an antibody prepared using the peptide has vastly superior detection sensitivity compared to existing EN2 protein antibodies and thus can be useful in a diagnostic agent for diagnosing prostate cancer.

2 Claims, 17 Drawing Sheets

Specification includes a Sequence Listing.

FIG. 1 homeobox protein engrailed-2 (EN-2) amino acid sequence

MEENDPKPGEAAAAVEGQRQPESSPGGGSGGGGGSSPGEADTGRRRA
LMLPAVLQAPGNHQHPHRITNFFIDNILRPEFGRRKDAGTCCAGAGGGR
GGGAGGEGGASGAEGGGGAGGSEQLLGSGSREPRQNPPCAPGAGGP
LPAAGSDSPGDGEGGSKTLSLHGGAKKGGDPGGPLDGSLKARGLGGG
DLSVSSDSDSSQAGANLGAQPMLWPAWVYCTRYSDRPSSGPRSRKPK
KKNPNKEDKRPRTAFTAEQLQRLKAEFQTNRYLTEQRRQSLAQELSLNE
SQIKIWFQNKRAKIKKATGNKNTLAVHLMAQGLYNHSTTAKEGKSDSE

Peptide 1, 151-180 a.a.
Peptide 2, 219-248 a.a.
Peptide 3, 230-258 a.a.

Company A antigen : 243-271 a.a. peptide
Company B antigen : partial recombinant EN2

Peptide 1

Peptide 2

FIG. 8C
Peptide 3
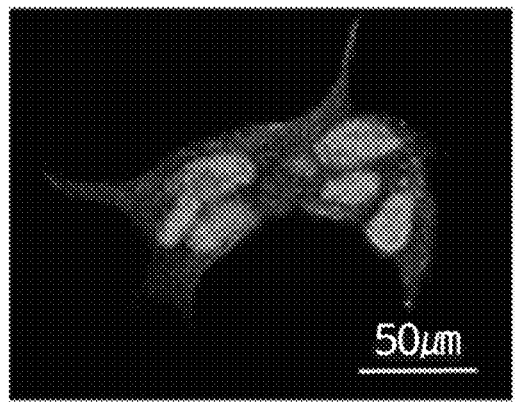
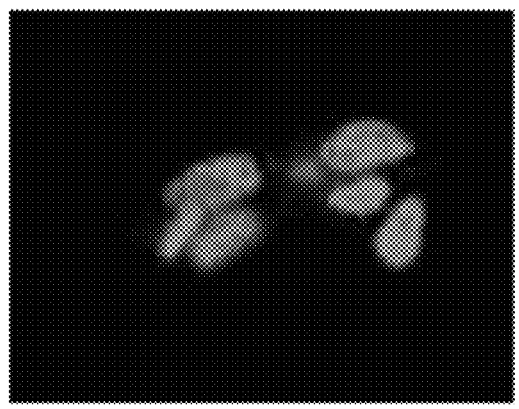
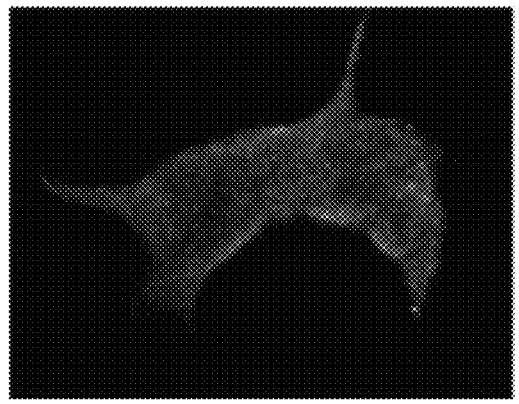

ANTIBODY COMPOSITION SPECIFICALLY RECOGNIZING AN IMMUNOGENIC FRAGMENT PEPTIDE OF EN2 PROTEIN

CROSS REFERENCE TO RELATED APPLICATIONS

This application is a division of U.S. application Ser. No. 16/488,238, filed on Aug. 22, 2019, which was a National Stage application of PCT/KR2017/013631, filed on Nov. 28, 2017, and claims priority to and the benefit of Korean Patent Application No. 10-2017-0024006 filed on Feb. 23, 2017, the contents of which are incorporated herein by reference.

TECHNICAL FIELD

The present invention relates to an immunogenic fragment peptide of an EN2 protein or an antibody composition specifically recognizing the same.

BACKGROUND ART

The prostate is a walnut-sized male reproductive organ beneath the bladder and in front of the rectum, and functions to create semen and store a portion thereof. The upper part of the prostate is adjacent to the bladder neck that connects from the bladder to the urethra and is fixed to the anterior puboprostatic ligament, and the lower part thereof is fixed by the genitourinary diaphragm. Most cancer that occurs in the prostate is adenocarcinoma (gland cell carcinoma) that forms in prostate cells. The types of cancer may be classified depending on the degree of differentiation of the tumor tissue and the characteristics of the cells.

Prostate cancer is one of the most common genitourinary tumors in the world. In the United States, about 180,890 persons were newly diagnosed with prostate cancer in 2016, accounting for 10.7% of all new tumor diagnoses in the United States, and prostate cancer, following breast cancer and lung cancer, is the third most frequently occurring kind of tumor. Based on worldwide statistics from 2009 to 2013, 129.4 men among 100,000 men have prostate cancer, and, based on statistics from 2016, 26,120 prostate cancer patients died. Moreover, prostate cancer is an uncommon disease before age 50, but shows a rapid increase after age 50. Recently, the number of aged men is drastically increasing in Korea due to the prolongation of the life expectancy and thus continuous management is required in order to prevent aggravation of the prostate cancer, such as metastasis, etc., through early diagnosis.

In particular, human prostate cancer appears to have a tendency to metastasize to the bone, and is known to inevitably progress from an androgen-dependent state to an androgen-resistant state, thereby increasing a patient mortality rate. Furthermore, about 25% of men who have undergone prostate cancer therapy require additional treatment due to recurrence of the disease, and prostate cancer is currently the second leading cause of cancer-related death in men in the United States. Hence, early diagnosis and treatment of prostate cancer is necessary.

Examples of a direct prostate cancer diagnosis method currently in use include a method of directly imaging the prostate or a biopsy diagnosis method. In the case of diagnosis through direct imaging or biopsy, it is difficult to diagnose the onset of prostate cancer at the initial stage, and thus it is urgently necessary to develop a method for in-vitro diagnosis.

As an indirect method, there is a diagnosis method that may be performed in vitro using a prostate-specific antigen (PSA) assay. However, the PSA used for diagnosis is produced not only in malignant prostate epithelium but also in normal and benign tissues, resulting in a high false-positive rate in prostate cancer detection. In addition, a significant increase in serum PSA level may be used for an effective standard method for diagnosing prostate cancer, whereas a weak increase in PSA serum level on the order of 2 to 10 ng/mL makes it impossible to reach a definite prostate cancer diagnosis. In the case of such a weak increase, the serum PSA may originate from a non-tumorous disease such as benign prostatic hyperplasia (BPH), prostatitis or other physical trauma, and PSA analysis for prostate cancer diagnosis has problems related to detection specificity.

Accordingly, diagnosis of prostate cancer using a new biomarker is regarded as important, and research thereon has been conducted (Korean Patent Application Publication No. 10-2009-0111307) but is still insufficient. Recently, methods of diagnosing prostate cancer using EN2 (engrailed-2) as a biomarker have been proposed, and EN2 is well known as a biomarker that is capable of solving the detection specificity problem of PSA (prostate specific antigen) assay used in conventional prostate cancer diagnosis. EN2 protein acts as a transcription factor in cells and is overexpressed only in prostate cancer cells, undesirably causing a DNA transcriptional regulatory disorder. Furthermore, when EN2 expression increases in prostate cancer cells, the amount of EN2 protein that is excreted by the urine is also increased, whereby EN2 is suitable for use in in-vitro analysis. Accordingly, U.S. Pat. No. 8,460,882, Japanese Patent Application Publication No. 2012-532621 and U.S. Pat. No. 8,722,643 disclose a diagnostic composition recognizing an EN2 protein, and Korean Patent Application Publication No. 10-2016-0077788 discloses a DNA aptamer specifically binding to EN2.

Generally, the term "antibody" means that an external substance (a substance having at least a predetermined size and conditions) (an antigen) is injected into an organism, and an antibody having a site (epitope) capable of specifically recognizing the external substance through a humoral immune response is formed in the organism, and is then collected from the blood and separated from the serum. The antibody thus formed is a polyclonal antibody having multiple sites capable of recognizing the antigen.

In the humoral immune response, antigens are presented to B cells through epitopes by various antigen-presenting cells (APC) and activate B cells. During the activation process, B cells are differentiated into plasma cells that enable only a single antibody to be produced in a large amount and secreted ex vivo by rearranging only the genes that make the antibody that is able to react with the antigen, among the whole genes that make the antibody, and removing the remaining unnecessary genes.

Since antigens typically have multiple epitopes, there are various kinds of differentiated plasma cells, and thus various antibodies are produced. The entire set of diverse antibodies secreted from various kinds of plasma cells (i.e. genes that make the antibody are different) is called a "polyclonal antibody", and only a single antibody made from one kind of plasma cell is called a "monoclonal antibody".

The market for diagnostic products using antibodies has been rapidly increasing since 1980, and antibodies are highly sensitive enough to detect very small amounts of proteins specifically expressed depending on diseases or symptoms, and thus are utilized for the development of highly efficient diagnostic kits and diagnosis methods. To this end, it is essential to develop an antibody that has both specificity and sensitivity to a protein (antigen) expressed depending on diseases or symptoms. In order to produce antibodies having specificity and sensitivity, the efficiency of the antibody may be maximized by considering several factors.

First, the primary sequence of an antigen to be produced is compared, and thus an animal to be immunized, having high heterogeneity from animal species of the antigen, is selected, thereby maximizing the immune response. For example, when the sequence of a human protein is used, an animal having high heterogeneity from the above sequence may be selected for induction of an immune response, thereby obtaining a high-titer antibody.

Second, selection is performed taking into consideration the fact that the quality of the antigen may vary depending on the characteristics of the modification after translation of the antigen sequence and on the stereostructure. In particular, selection has to be conducted considering the case where not the whole protein but some peptide form thereof is used as an antigen.

Third, the antibody is prepared so as to be adapted for the purpose thereof. A polyclonal antibody is advantageous because it is easy to produce, facilitates the detection of an antigen due to the wide variety of epitopes thereof, and enables selection of animals to be immunized from among a wide range depending on the antigen, but is low in antibody specificity and is unsuitable for mass production of a consistent titer. Also, a monoclonal antibody has the advantage of producing antibodies in culture supernatants to thus enable mass production of antibodies having specificity of a consistent titer but is disadvantageous in that it takes a long period of production, is limited with respect to the range of animals capable of being immunized, and is not suitable for experiments such as immunological staining.

Therefore, in general, the specificity of the antigen is confirmed through the production of a polyclonal antibody, and a monoclonal antibody is prepared when mass production of an antibody having a consistent titer is required.

Meanwhile, the present inventors have studied compositions related to the diagnosis of prostate cancer and have prepared a composition for diagnosing prostate cancer based on an EN2 protein fragment capable of more effectively diagnosing an EN2 protein or an antibody capable of recognizing the fragment, thus culminating in the present invention.

CITATION LIST (Patent Document 1) U.S. Pat. No. 8,460,882 (Title: Cancer biomarkers, Applicant: The University of Surrey, Registration date: Jun. 11, 2013)
(Patent Document 2) U.S. Pat. No. 8,722,643 (Title: Targeting EN2, PAX2, and/or DEFB1 for treatment of prostate conditions, Applicant: Phigenix, Inc., Registration date: May 13, 2014)
(Patent Document 3) Japanese Patent Application Publication No. 2012-532621 (Title: Therapeutic peptide, polypeptide and nucleic acid array, Applicant: The University of Surrey, Laid-open date: Dec. 20, 2012)
(Patent Document 4) Korean Patent Application Publication No. 10-2009-0111307 (Title: DNA aptamer specifically binding to EN2 and use thereof, Applicant: POSTECH Research and Business Development Foundation, Laid-open date: Jul. 4, 2016)
(Patent Document 5) Korean Patent Application Publication No. 10-2016-0077788 (Title: Prostate-specific transcripts and their use in the treatment and diagnosis of prostate cancer, Applicant: Exxon Heat Therapeutics SA, Laid-open date: Oct. 26, 2009)

DISCLOSURE

Technical Problem

Accordingly, the present invention is intended to provide an immunogenic fragment peptide of an EN2 protein or an antibody composition specifically recognizing the same.

Technical Solution

The present invention provides a peptide comprising the amino acid sequence of SEQ ID NO: 1, 2 or 3 below.

```
SEQ ID NO: 1:
PGDGEGGSKTLSLHGGAK
KGGDPGGPLDGS

SEQ ID NO: 2:
CTRYSDRPSSGPRSRKPKKKNPNKEDKRPR

SEQ ID NO: 3:
PRSRKPKKKNPNKEDKRPRTAFTAEQLQR
```

The peptide may be an immunogenic fragment of EN2 (engrailed-2) protein (Accession No. NP_001418.2).

Thus, the present invention provides a method of diagnosing the presence or absence of EN2 (engrailed-2) protein by specifically recognizing the above peptide.

In addition, the present invention provides an antibody composition specifically recognizing each peptide comprising the amino acid sequence of SEQ ID NO: 1, 2 or 3.

Thus, the present invention provides a diagnostic agent for diagnosing prostate cancer containing the above antibody composition.

Thus, the present invention provides a method of diagnosing prostate cancer using the above antibody.

Hereinafter, a detailed description will be given of the present invention.

The present invention pertains to a peptide comprising the amino acid sequence of SEQ ID NO: 1, 2 or 3 below.

```
SEQ ID NO: 1:
PGDGEGGSKTLSLHGGAKKGGDPGGPLDGS

SEQ ID NO: 2:
CTRYSDRPSSGPRSRKPKKKNPNKEDKRPR

SEQ ID NO: 3:
PRSRKPKKKNPNKEDKRPRTAFTAEQLQR
```

In the present invention, commercially available antibodies, serving as comparative examples, are those prepared using, as an antigen, a peptide comprising the amino acid sequence of SEQ ID NO: 4 or 5 below.

```
SEQ ID NO: 4:
EDKRPRTAFTAEQLQRLKAEFQTNRYLTE

SEQ ID NO: 5:
GTCCAGAGGGRGGGAGGEGGASGAEGGGGAGGSEQLLGSGSREPRQNPPC

APGAGGPLPAAGSDSPGDGEGGSKTLSLHGGAKKGGDPGGPLDGSLKARG

LGGGDLSVSSDSDSSQAGANLGAQP
```

The positions of these peptides in EN2 are shown in FIG. 1.

The peptide comprising the amino acid sequence of SEQ ID NO: 1, 2 or 3 is an immunogenic fragment of an EN2 protein and is an EN2 protein fragment having at least one epitope that may be recognized by an antibody for an EN2 protein, a quantity of which increases or decreases in the body of a prostate cancer patient.

The present invention pertains to a method of diagnosing the presence or absence of an EN2 protein by specifically recognizing the above peptide. Here, the EN2 protein may be any example thereof extracted from the inside of a mammal to the outside, and may also be a recombinant EN2 protein. In order to evaluate the presence or absence of an EN2 protein, any method may be used, so long as it is an ordinary experimental method used to determine the presence or absence of a protein or in the quantification process thereof.

In addition, the present invention pertains to an antibody composition specifically recognizing each peptide comprising the amino acid sequence of SEQ ID NO: 1, 2 or 3 or to a diagnostic agent containing the same. The diagnostic agent may also contain a labeled secondary antibody, a chromophore, an antibody-conjugated enzyme and an additional substance able to bind to the substrate or antibody thereof.

When the diagnostic agent contains all of respective antibodies for three types of peptides comprising the amino acid sequences of SEQ ID NOS: 1, 2 and 3, prostate cancer may be more accurately diagnosed compared to when using a diagnostic agent containing any one or two antibodies. For example, in order to identify the EN2 protein contained in the body of a subject to be diagnosed, samples collected from the subject to be diagnosed may be divided into three sets. For one set, the presence and concentration of EN2 protein are determined using an antibody against the peptide comprising the amino acid sequence of SEQ ID NO: 1, and for each of the remaining sets, the presence and concentration of EN2 protein are determined separately for respective antibodies against the peptide comprising the amino acid sequence of SEQ ID NO: 2 and against the peptide comprising the amino acid sequence of SEQ ID NO: 3, and a total of three EN2 protein detection experiments may be performed. In this way, when the EN2 protein is detected using the diagnostic agent, the accuracy and reliability of the diagnosis result may be increased.

Also, the diagnostic agent of the present invention may contain a recombinant EN2 protein able to quantify the EN2 protein contained in the body of the subject to be diagnosed.

An antibody is a specific protein molecule directed to an antigenic site. Therefore, the antibody is preferably an antibody that specifically binds to a peptide of the present invention, and may include all of a polyclonal antibody, a monoclonal antibody, and a recombinant antibody.

The antibody may be easily produced using techniques well known in the art. Accordingly, the present invention pertains to a method of preparing an antibody using the peptide of the present invention.

The polyclonal antibody may be obtained from the serum obtained by injecting an animal with the peptide of the present invention as an antigen. The animal may be any animal host such as goat, rabbit, pig and the like. The monoclonal antibody may be prepared using a hybridoma process (Kohler G. and Milstein C.) or a phage antibody library process (Clackson et al. Marks et al.), as widely known in the art to which the present invention belongs. The hybridoma process may be conducted using cells of an immunologically relevant host animal, such as a mouse, and a cancer or myeloma cell line. Then, through a process using polyethylene glycol, as widely known in the art to which the present invention belongs, the two kinds of cells are fused, after which the antibody-producing cells may be proliferated through a standard tissue culture process. Then, a uniform cell population is obtained through subcloning using a limited dilution technique, after which hybridoma capable of producing an antibody specific to the peptide of the present invention may be mass-cultured in vitro or in vivo using a standard technique. The phage antibody library process may be performed in a manner in which an antibody gene for the peptide of the present invention is obtained and expressed in the form of a fusion protein on the surface of a phage to thus manufacture an antibody library in vitro, after which a monoclonal antibody that binds to the peptide of the present invention is separated from the library and thus produced. The antibody thus produced may be separated through centrifugation, electrophoresis, dialysis, ion exchange chromatography, affinity chromatography, and the like.

The antibody may comprise a functional fragment of an antibody molecule as well as a complete form having two full-length light chains and two full-length heavy chains. A functional fragment of an antibody molecule is a fragment having at least an antigen-binding function, and includes Fab, F(ab'), F(ab')2, F(ab)2, Fv and the like.

In addition, the present invention pertains to a method of preparing the antibody, which is described below.

Preferably, the method includes (step 1) preparing an antigen for antibody production by linking the peptide of the present invention with a carrier protein using a crosslinker;

(step 2) mixing and emulsifying the antigen with an adjuvant;

(step 3) intradermally injecting the antigen containing the emulsified adjuvant to an animal two to five times at an interval of 7 to 20 days;

(step 4) separating the serum from the whole blood of the animal 7 to 20 days after antigen administration; and (step 5) separating and purifying an immunoglobulin from the serum.

In the method of preparing the antibody as above, the animal may be any animal capable of causing an immune response, and is preferably a mammal. The immunoglobulin in step 5 may be of any type, but is preferably immunoglobulin G.

When the immune response is induced using peptide 1, 2 or 3 in order to prepare the antibody of the present invention, the peptide 1, 2 or 3 is linked with the carrier protein using the crosslinker and may thus be used as an antigen. Here, the carrier protein may include BSA, KLH, OVA, etc., having low antigenicity and being responsible only for a carrying function, and the crosslinker for connecting the peptide and the protein may include EDC, glutaraldehyde (linkage of carrier molecules to N-terminus of peptide), succinimide esters (e.g. MBS, SMCC), benzidine (BDB) (linkage to Tyr residues), periodate (attachment to carbohydrate groups), isothiocyanate (used to label antibodies with fluorochromes), etc. As such, a buffer solution may be used in a variety of manners depending on the characteristics of the linker that is used.

In addition, the present invention pertains to a method of diagnosing prostate cancer using the peptide of the present invention or the antibody specifically recognizing the same.

The diagnosis method includes:

(step 1) separating a body protein from a sample to be analyzed;

(step 2) forming an antigen-antibody complex by bringing the body protein of step 1 into contact with the antibody of the present invention; and (step 3) quantitatively detecting and analyzing the antigen-antibody complex formed in step 2.

In the diagnosis method, the sample of step 1 may be extracted from a subject for whom the occurrence or progression of prostate cancer is to be confirmed, and preferable examples thereof include tissue, cells, etc. of a mammal (human or other animals), and more preferable examples thereof include urine, blood, plasma, serum, and liver cells.

Separating the body protein in step 1 may be performed using any known process, and the amount of the body protein may be measured through any of various methods known to those skilled in the art.

The antigen-antibody complex of step 2 is configured such that the EN2 protein contained in the body protein of the sample (or Peptide 1, 2 or 3 of the present invention) and the antibody are specifically bound to each other. In the complex, the antigen means the EN2 protein (or Peptide 1, 2 or 3 of the present invention).

Through the above analysis method, the amount of the antigen-antibody complex formed in the case of a control and the amount of the antigen-antibody complex formed in the case of the subject for whom the occurrence or progression of prostate cancer is to be confirmed may be compared, and the expression level of the EN2 protein of the subject for whom the occurrence or progression of prostate cancer is to be confirmed is determined, and thus prostate cancer may be directly diagnosed.

In step 3, the amount of EN2 of the sample of the subject for whom the occurrence or progression of prostate cancer is to be confirmed may be determined based on the standard value in which the concentration of the recombinant EN2 protein is measured. Here, detection of EN2 protein in vivo using all of three antibodies, rather than one or two antibodies, is most preferable. In detail, protein taken from the sample may be divided into three sets, and respective antibodies may react with proteins corresponding to respective sets, whereby EN2 may be detected.

The expression level of the EN2 protein of the subject for whom the occurrence or progression of prostate cancer is to be confirmed may be determined by measuring whether it falls in the range of 3.1 to 65.4 nM (Sci. Rep. 2013; 3:2059), which is the known concentration range of EN2 protein in the urine of prostate cancer patients.

The amount of the antigen-antibody complex that is formed may be quantitatively measured based on the signal magnitude of a detection label. The detection label may be selected from the group consisting of an enzyme, a fluorescent substance, a ligand, a luminescent substance, microparticles, a redox molecule and a radioisotope, but the present invention is not limited thereto. When an enzyme is used as the detection label, examples of the enzyme include, but are not limited to, β-glucuronidase, β-D-glucosidase, β-D-galactosidase, urease, peroxidase, alkaline phosphatase, acetylcholinesterase, glucose oxidase, hexokinase and the like. Examples of the fluorescent substance include, but are not limited to, fluorescein, phycocyanin, fluorescamine and the like. Examples of the ligand include, but are not limited to, biotin derivatives, etc. Examples of the luminescent substance include, but are not limited to, luciferin and the like. Examples of the microparticles include, but are not limited to, colloids, gold and the like. Examples of the redox molecule include, but are not limited to, quinone, 1,4-benzoquinone, hydroquinone and the like. Examples of the radioisotope include, but are not limited to, $^3H$, $^{14}C$ and the like.

Examples of the diagnosis method may include, but are not limited to, western blot, ELISA (enzyme linked immunosorbent assay), RIA (radioimmunoassay), radioimmunodiffusion, ouchterlony immunodiffusion, rocket immunoelectrophoresis, immunohistochemistry, immunoprecipitation, complement fixation assay, FACS (fluorescence-activated cell sorter), protein chip, etc.

As a subject to be diagnosed, to which the peptide or antibody of the present invention may be applied, any subject may be used so long as an EN2 protein may be produced in vivo, and diagnosis is possible for all mammals, including humans. The mammal may be any type of mammal, such as a human, a dog, a cat, a rabbit, cattle, a goat, a pig, a horse, etc.

Advantageous Effects

The present invention pertains to an immunogenic fragment peptide of an EN2 protein or an antibody composition specifically recognizing the same. In the present invention, quantification of the EN2 protein becomes possible through a method of specifically recognizing the peptide. In addition, the antibody prepared using the peptide is very high in detection sensitivity compared to existing EN2 protein antibodies, and can thus be efficiently used in a diagnostic agent for diagnosing prostate cancer. In particular, when prostate cancer is diagnosed, high diagnostic efficacy can result compared to results of PSA (prostate-specific antigen) detection in the blood, which is a conventional prostate cancer diagnosis method.

BRIEF DESCRIPTION OF DRAWINGS

FIG. 1 schematically shows, in the entire peptide sequence of homeobox protein engrailed-2 (EN2), three types of peptide sequences used as antigens and antigen peptide sequences for commercially available antibodies (the peptide of SEQ ID NO: 1: Peptide 1; the peptide of SEQ ID NO: 2: Peptide 2; the peptide of SEQ ID NO: 3: Peptide 3; the peptide of SEQ ID NO: 4: Antigen for preparing Company A antibody; and the peptide of SEQ ID NO: 5: Antigen for preparing Company B antibody);

FIG. 8A, FIG. 8B and FIG. 8C show the results of immunocytochemistry testing of the detection of the purified antibody using recombinant EN2 protein;

MODE FOR INVENTION

Figure 2:
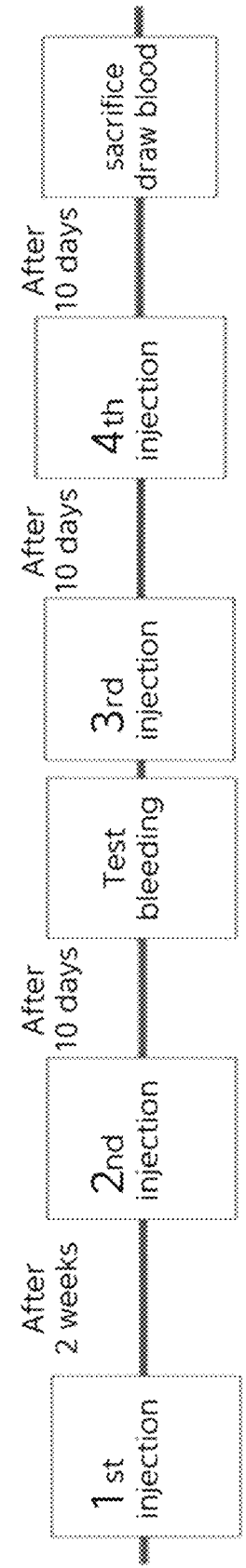
FIG. 2 schematically shows the overall timetable for an immunized animal in which an immune response is induced.

A better understanding of preferred embodiments of the present invention will be given through the following examples. However, the present invention is not limited to these examples but may be embodied in other forms. These examples are provided to thoroughly explain the invention and to sufficiently transfer the spirit of the present invention to those skilled in the art.

Example 1. EN2 Peptide Selection, Synthesis and Antigen Preparation

Example 1-1. Selection of Amino Acid Sequence of Peptide Serving as Antigen and Synthesis of Peptide Using a professional antibody company program (Antigen profiler peptide tool—Thermo Fisher Scientific), the entire protein sequence of EN2 was cut into peptides 30 amino acids long, and each peptide was scored for antigenicity ranging from 1 to 5 based on an antigenic index, among which regions having a score of 3.8 or higher were selected. Here, the antigenic index is a measure of the probability that nucleotides are antigenic depending on the structural effect, the stereostructure and the like caused by modification after translation thereof into proteins.

Among the regions thus selected, regions in which many hydrophobic residues were distributed were excluded from the selection because external exposure is blocked in the folded protein structure, and among the top 10 peptides that scored most highly in the sequences of the peptides selected based on the above criteria, three peptides having a small number of hydrophobic residues were selected.

The above three peptides were requested to be synthesized in 10 mg at 98% purity (Anigene, Korea), and peptides comprising the amino acid sequences of SEQ ID NOS: 1 to 3 were obtained. The positions of the peptide sequences thus synthesized in the EN2 protein are shown in FIG. 1.

```
SEQ ID NO: 1:
PGDGEGGSKTLSLHGGAKKGGDPGGPLDGS

SEQ ID NO: 2:
CTRYSDRPSSGPRSRKPKKKNPNKEDKRPR

SEQ ID NO: 3:
PRSRKPKKKNPNKEDKRPRTAFTAEQLQR
```

Example 1-2. Linkage of Carrier Protein and Peptide

The three peptides prepared in Example 1-1 have small sizes, and when these peptides are directly used as antigens, it is difficult to induce an immune response, and thus each peptide was linked with a carrier protein (KLH (keyhole limpet hemocyanin)) using a crosslinker.

Particularly, each peptide, a carrier protein, and a crosslinker were dissolved at a weight ratio of 1:1:1 and allowed to sufficiently react at room temperature for 2 hr or more. As such, the crosslinker was EDC (1-ethyl-3-[3-dimethylaminopropyl]carbodiimide hydrochloride), and as a binding buffer, 0.1 M MES (2-[N-morpholino]ethane sulfonic acid) (pH 4.5 to 5) was used (the buffer functions to induce hydrolysis of an amine group).

After termination of the reaction, the bound material and the unbound material were separated from each other using a Thermo Scientific Zeba Spin Desalting Column (#89891) based on a size difference therebetween (KLH 400 kD and peptide 3.5 kD, based on the size difference between a bound material and an unbound material).

Then, the peptide thus linked with the carrier protein was used as an antigen for antibody preparation.

Example 1-3. Preparation of Antigen Emulsified with Adjuvant

In order to administer an antigen to an animal to be immunized, an antigen having high solubility is required to be coupled with an adjuvant so as to reside for a long period of time in vivo, and thus a composition in which an adjuvant and an antigen were emulsified was prepared.

Also in order to induce an effective immune response, the antigen prepared in Example 1-2 was administered a total of four times, and the antigen for first administration was prepared by mixing a Freund's complete adjuvant (FCA) containing killed *mycobacterium* in order to maximize an immune response, and the antigens for the remaining three administrations were prepared by mixing a Freund's incomplete adjuvant (FIA) excluding killed *mycobacterium*.

Here, in order to effectively emulsify the water-soluble antigen and the hydrophobic adjuvant, the antigen and the adjuvant were mixed through probe sonication, and the temperature was maintained at 4° C. so as not to apply heat to the antigen during the mixing. The antigen and the adjuvant were mixed at a volume ratio of 1:1.

Example 2. Induction of Immune Response Using Antigen

Example 2-1. Selection of Animal to be Immunized

Rats (Wistar) were used as animals in order to induce an immune response to a human EN2 protein sequence. An immune response was induced in nine 7-week-old female individuals for each peptide sequence in consideration of individual specificity, because the immune response may vary depending on individuals.

Example 2-2. Experimental Timetable and Injection Method for Immunized Animal

The overall timetable for immunity induction followed the procedure of FIG. 2, in which the antigen was first administered and was administered again after 2 weeks, after which the antigen was further administered two times at an interval of 10 days, whereby a total of four administrations was performed. The extent of immune response was checked through tail vein bleeding after the second administration (test bleeding). Intradermal injection was used as the method of administration, and 2 to 3 locations were selected at the time of a single administration, and a total of 200 μL was injected per individual.

Example 3. Separation of Serum from Immunized Animal and Purification of Immunoglobulin G (IgG)

Example 3-1. Separation of Serum from Immunized Animal

The immunized animals administered with the antigen in Example 2-2 were sacrificed as shown in FIG. 2. Whole blood was obtained through abdominal vena cava blood collection using an inhalation anesthetic (Isoflurane). The whole blood was maintained at 37° C. for 1 hr and then centrifuged at 2000 rpm for 20 min, and 4 to 5 mL of serum per individual was obtained from the centrifuged supernatant.

Example 3-2. Separation of Immunoglobulin G (IgG)

Since the serum contains various proteins including albumin, immunoglobulin G (IgG) was purified alone in order to increase the titer and specificity of the antibody.

Separation and purification were performed using a resin coupled with protein G specifically binding to rat IgG (Protein G Sepharose 4 Fast Flow—GE Healthcare). The separated serum was diluted with a buffer (PBS) at a volume ratio of 1:1, bound to the packed resin, and washed with a buffer in a volume corresponding to 2 to 3 times the volume of beads and then eluted.

As an elution buffer, a buffer having a pH of 2 to 3 was used to break the specific binding of protein G and IgG. In order to raise the pH to a normal level immediately after elution, Tris (pH 9) was used.

Figure 3A:
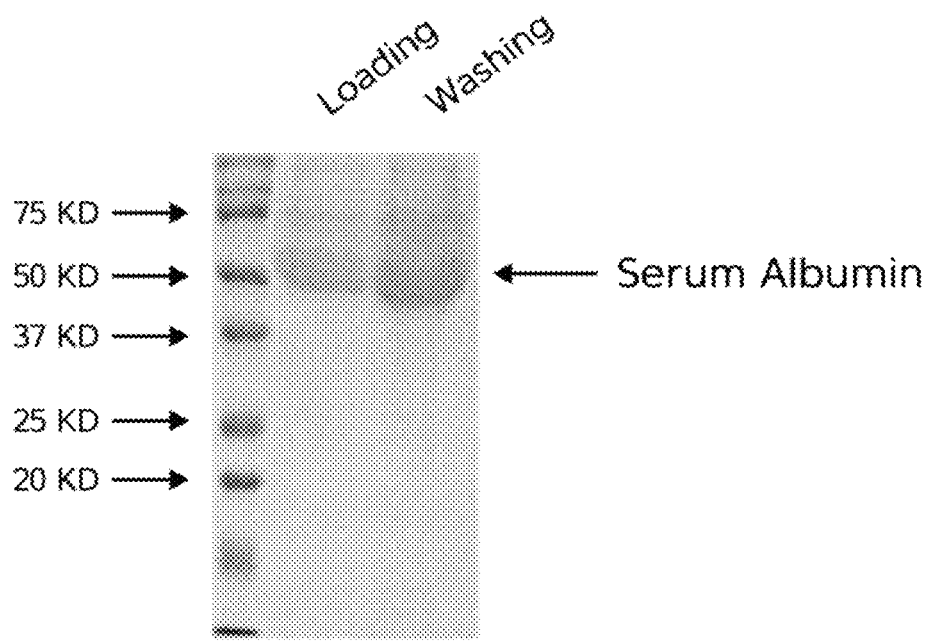
FIG. 3A, FIG. 3B AND FIG. 3C show the results of SDS-PAGE of samples separated and purified from the immunized animal serum.
Figure 3B:
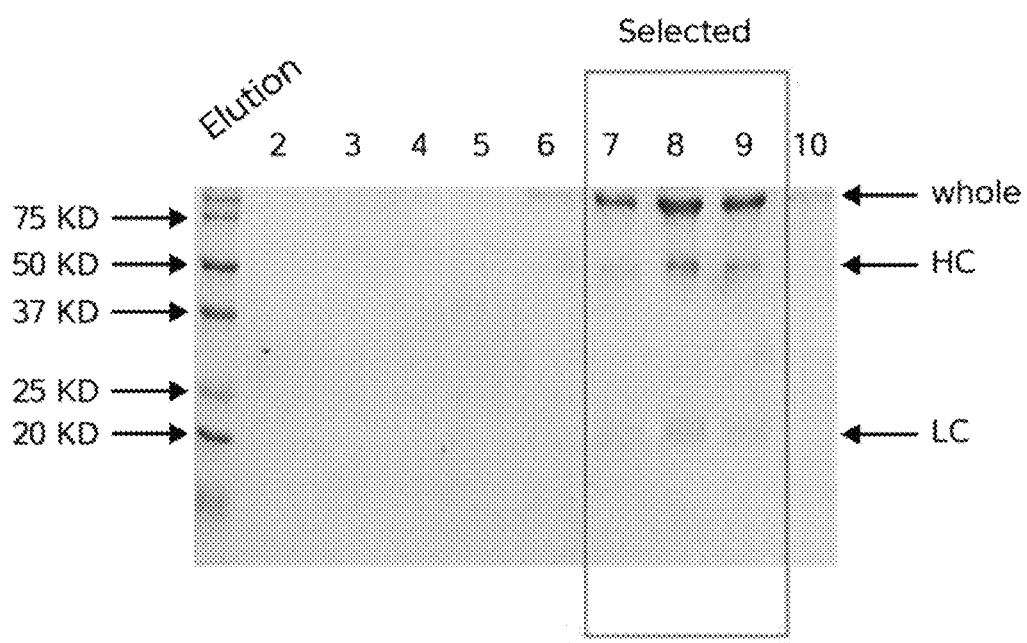
Figure 3C:
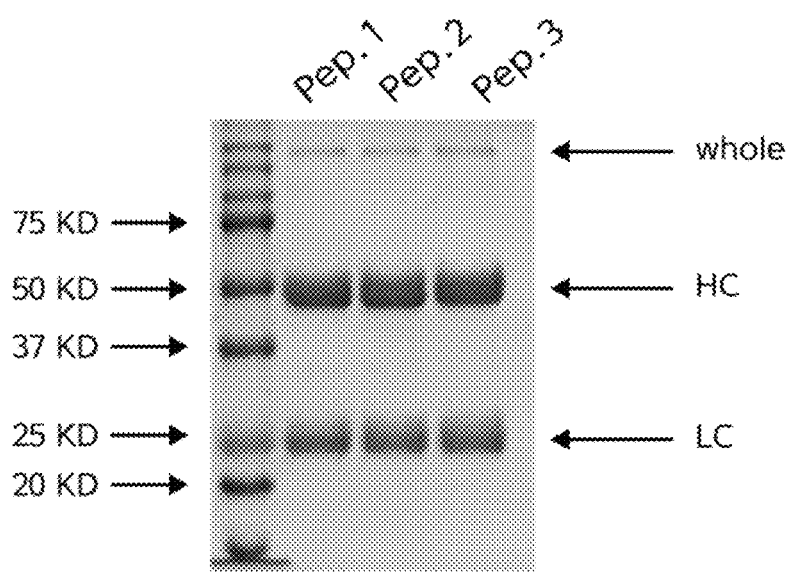

The serum was eluted into 10 fractions, and as is apparent from the SDS-PAGE gel, IgG was obtained from 7 to 9 fractions (FIGS. 3a and 3b show the results of Peptide 3, and specifically show that the serum sample identified through the serum albumin was fractionated in FIG. 3a and thus the presence of IgG was confirmed in FIG. 3b). For each peptide, as shown in FIG. 3c, final IgG was found to have high purity by removing other proteins from the serum per peptide (Whole: whole antibody, HC: heavy chain of antibody, LC: light chain of antibody). The antibody (IgG) of each of the finally obtained peptides was quantified, diluted with a PBS/0.2% sodium azide/20% glycerol buffer, aliquoted and stored at −80° C. Here, the amount of IgG obtained for respective peptide sequences and individuals is shown in Table 1 below.

TABLE 1

| Ag | Mouse | Conc. (mg/mL) | Volume (μL) |
|---|---|---|---|
| EN2-1 | 1 | 10 | 500 |
|  | 2 | 10 | 300 |
|  | 3 | 10 | 500 |
|  | 4 | 10 | 500 |
|  | 5 | 3 | 500 |
|  | 6 | 10 | 500 |
|  | 7 | 10 | 500 |
|  | 8 | 10 | 500 |
|  | 9 | 10 | 500 |
| EN2-2 | 1 | 10 | 500 |
|  | 2 | 10 | 300 |
|  | 3 | 8 | 300 |
|  | 4 | 10 | 500 |
|  | 5 | 10 | 500 |
|  | 6 | 10 | 500 |
|  | 7 | 10 | 300 |
|  | 8 | 10 | 500 |
|  | 9 | 10 | 300 |
| EN2-3 | 1 | 10 | 500 |
|  | 2 | 10 | 300 |
|  | 3 | 10 | 500 |
|  | 4 | 10 | 500 |
|  | 5 | 5 | 500 |
|  | 6 | 5 | 300 |
|  | 7 | 10 | 500 |
|  | 8 | 7 | 300 |
|  | 9 | 10 | 500 |

Example 4. Expression and Purification of Recombinant Human EN2 Protein

In order to test the sensitivity and accuracy of the prepared antibody, recombinant EN2 protein was prepared. Particularly, pET28b/EN2 plasmid was transformed into *Escherichia coli* (BL21/DE3) and thus EN2 protein was overexpressed under conditions of 0.1 mM IPTG and 37° C. The overexpressed *Escherichia coli* cells were lysed through sonication with a lysis buffer (20 mM Tris-Cl at pH 8.0, 300 mM NaCl, 20 mM imidazole, a 1× protease inhibitor cocktail, 1 mg/mL lysozyme) and centrifuged, thus obtaining only a water-soluble protein. The water-soluble protein was affinity-bound to EN2/His Tag and Ni on Ni-NTA agarose beads. Thereafter, EN2 protein was isolated with an elution buffer (20 mM Tris-Cl at pH 8.0, 300 mM NaCl, 300 mM imidazole, a 1× protease inhibitor cocktail), and the imidazole was removed through dialysis (cutoff 10 K) in a storage buffer (50 mM Tris-HCl at pH 8.0, 200 mM KCl, 0.1 mM EDTA, 1 mM DTT, 0.5 mM PMSF, 20% glycerol), followed by BCA (bicinchoninic acid) quantification and protein concentration quantification at an absorbance of 280 nm.

Experimental Example 1. Evaluation of EN2 Protein Detection Ability in Prostate Cancer Cell Line (PC3 Cell Line)

A prostate cancer cell line PC3 (®CRL-1435™) for use in experiments was purchased from ATCC (American Type Culture Collection, Rockville, Md., USA) and cultured in a 5% $CO_2$ humidified incubator at 37° C. with a 25 mM HEPES-containing RPMI-1640 (PC3) or RPMI-1640 (LNCaP) medium added with 10% fetal bovine serum (FBS) and 1% penicillin/streptomycin (P/S).

The antigen detection ability of the antibody (obtained in Example 3) in a prostate cancer cell line PC3 having high EN2 expression was measured through western blotting assay. Here, the antibodies prepared in the present invention and commercially available EN2 antibodies (Company A, Company B) were compared and tested.

Company A: Thermo Fisher Scientific (PA5-14363)
Company B: Novus Biologicals (H00002020-M03)

Particularly, the cultured PC3 was lysed in a RIRA buffer containing a protease inhibitor cocktail and centrifuged at 12000 rpm for 20 min to collect the water-soluble protein, and the total protein content was determined through a BCA quantification method.

More particularly, $2 \times 10^6$ PC3 cells were cultured in 100 $cm^2$ culture dishes for 3 days and then washed two times with a cold PBS (phosphate buffered saline) solution to thus collect the cells, which were then lysed in ice for 30 min in a RIPA buffer solution containing a protease inhibitor cocktail. The cell lysate was centrifuged at 13,000 rpm for 20 min, and the protein concentration in the supernatant was measured through a BCA method, and the lysed proteins were separated using 4-15% SDS-PAGE. The proteins separated through PAGE were transferred to a PVDF membrane, and each EN2 antibody was diluted with 5% skim milk/ TBS-T (Tris-saline+Tween20) at a ratio of 1:2000 and reacted overnight at 4° C., and the next day washing was performed three times with TBS-T, and a horseradish peroxidase (HRP)-conjugated anti-RAT antibody was diluted with 5% skim milk/TBS-T at a ratio of 1:2000 and allowed to react at room temperature for 2 hr. The membrane washed three times with TBS-T was treated using an ECL (enhanced chemiluminescence) solution, and thus blue light emitted while luminol, which is a substrate of the peroxidase binding to the secondary antibody, was oxidized by the peroxidase was photosensitized to an X-ray film.

Figure 4A:
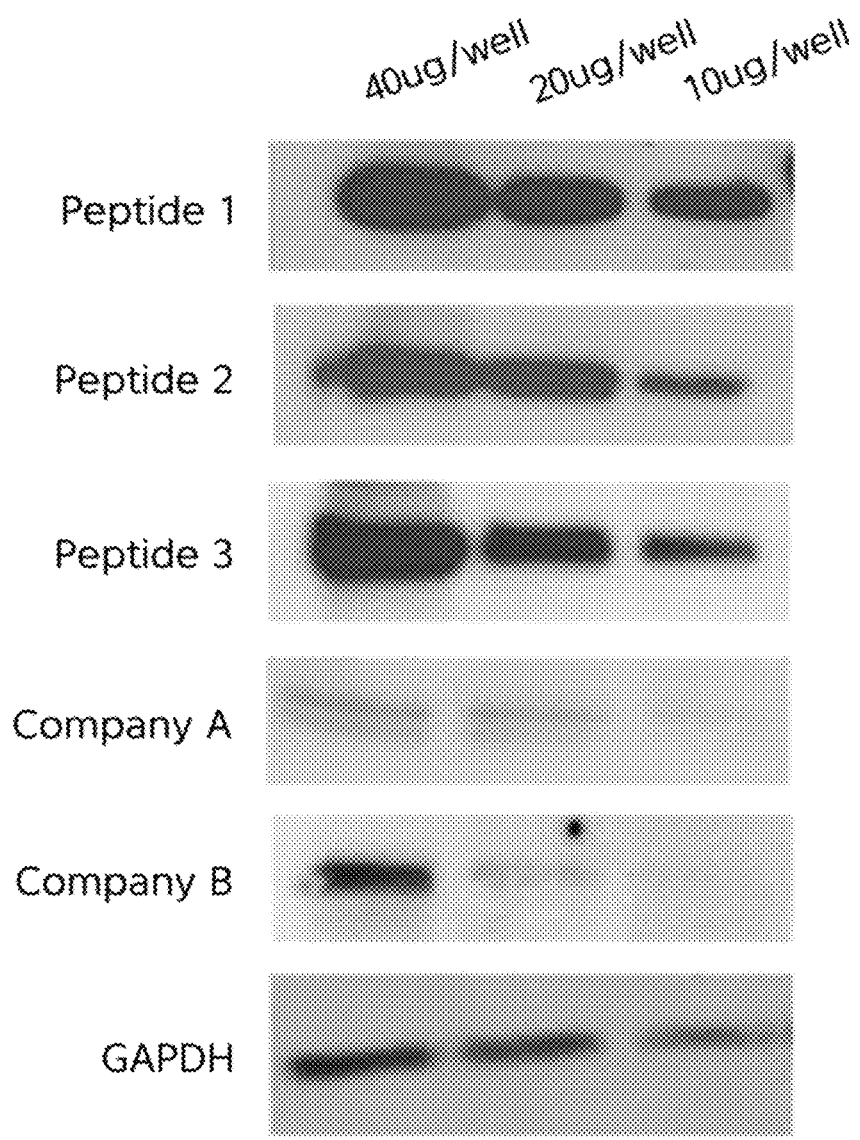
FIG. 4A and FIG. 4B show the results of western blotting assay of the selective detection for EN2 protein expressed in a prostate cancer cell line (PC3) (in FIG. 4, the antibody for the peptide of SEQ ID NO: 1 is represented as Peptide 1, Pep.1, the antibody for the peptide of SEQ ID NO: 2 is represented as Peptide 2, Pep.2, the antibody for the peptide of SEQ ID NO: 3 is represented as Peptide 3, Pep.3, the antibody for the peptide of SEQ ID NO: 4 is represented as Company A, ComA, and the antibody for the peptide of SEQ ID NO: 5 is represented as Company B, ComB)
Figure 4B:
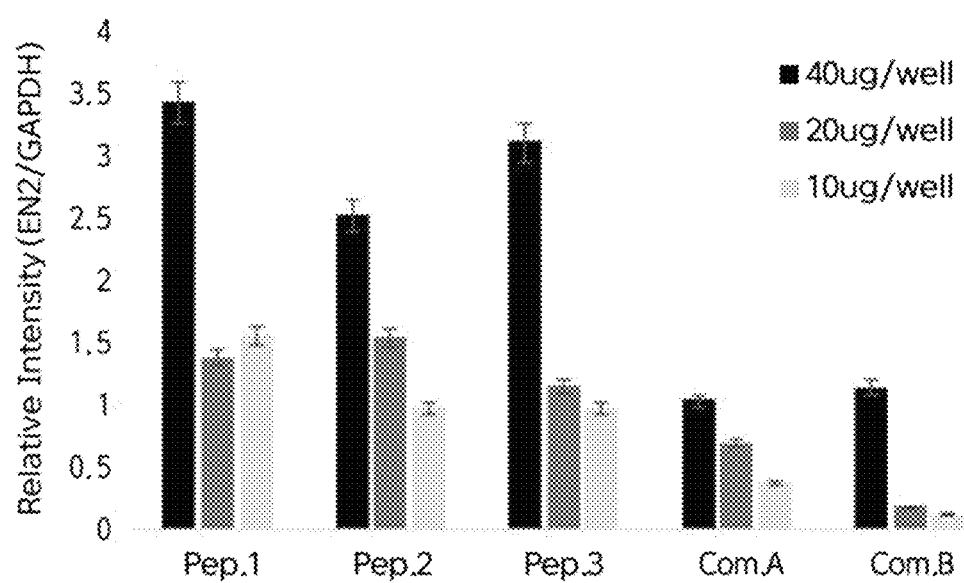

As such, 20 µL of whole protein extracted from the PC3 cells in an SDS-PAGE gel was loaded at 40 µg/well, 20 µg/well, and 10 µg/well in each well of a 96-well plate, followed by western blotting assay, after which the protein detection ability was measured using the antibodies (6.6 nM) having the same concentration. The results are shown in FIG. 4. FIG. 4a shows the band images obtained through western blotting, and FIG. 4b is a graph showing the numeric values of the results.

As shown in FIG. 4, the antibodies of the present invention (prepared in Example 3 using Peptides 1 to 3 as antigens) exhibited a very high ability to detect EN2 protein compared to commercially available antibodies (Company A, Company B) (under protein treatment conditions of 10 µg/well, the antibodies prepared using Peptides 1 to 3 as antigens exhibited detection ability 2 to 10 times as high as commercially available antibodies).

Experimental Example 2. Evaluation of EN2 Protein Detection Ability in Prostate Cancer Cell Line (LNCap Cell Line)

Figure 5A:
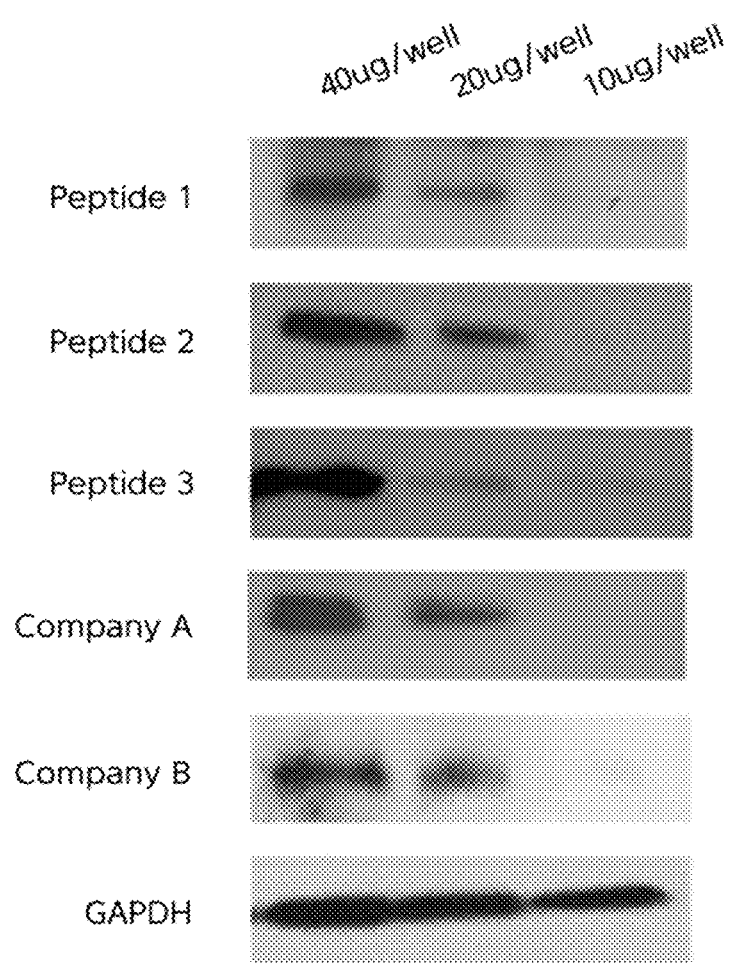
FIG. 5A and FIG. 5B show the results of western blotting assay of the selective detection for EN2 protein expressed in a prostate cancer cell line (LNCaP)
Figure 5B:
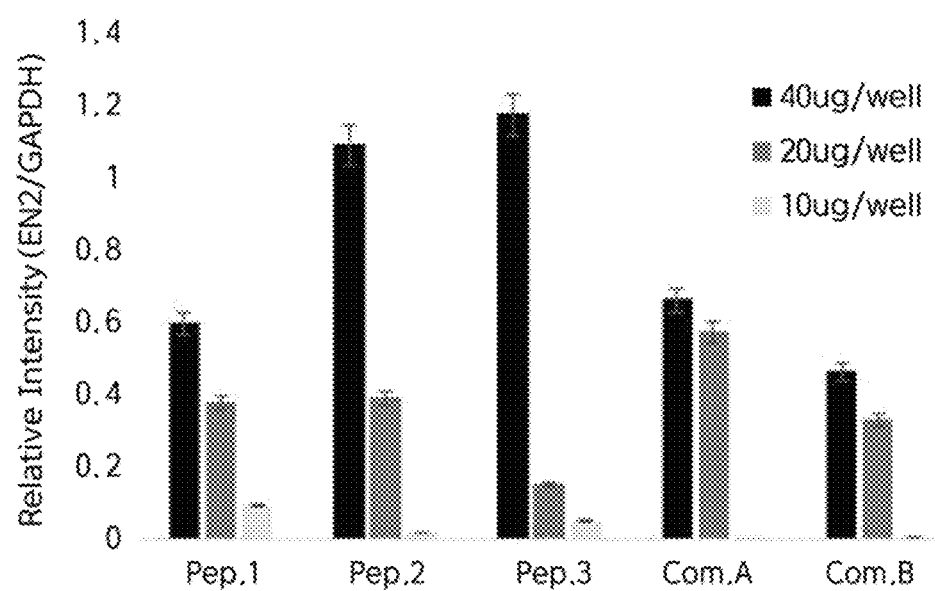

As another prostate cancer cell line known to have high EN2 expression, LNCaP (®CRL-1740™) cells were used, and the detection ability of the antibodies was evaluated under the same conditions as in Experimental Example 1. The results are shown in FIG. 5. FIG. 5a shows the band images obtained through western blotting, and FIG. 5b is a graph showing the numeric values of the results.

As shown in FIG. 5, compared to commercially available antibodies (Company A and Company B), the antibodies of the present invention (against Peptides 1 to 3 prepared in Example 3) exhibited superior selective antigen detection ability. Thus, based on the results of Experimental Examples 1 and 2, the antibodies prepared in Example 3 showed selective binding to the EN2 antigen, rather than cell-specific binding.

Experimental Example 3. Evaluation of Sensitivity Using Recombinant EN2 Protein

Figure 6A:
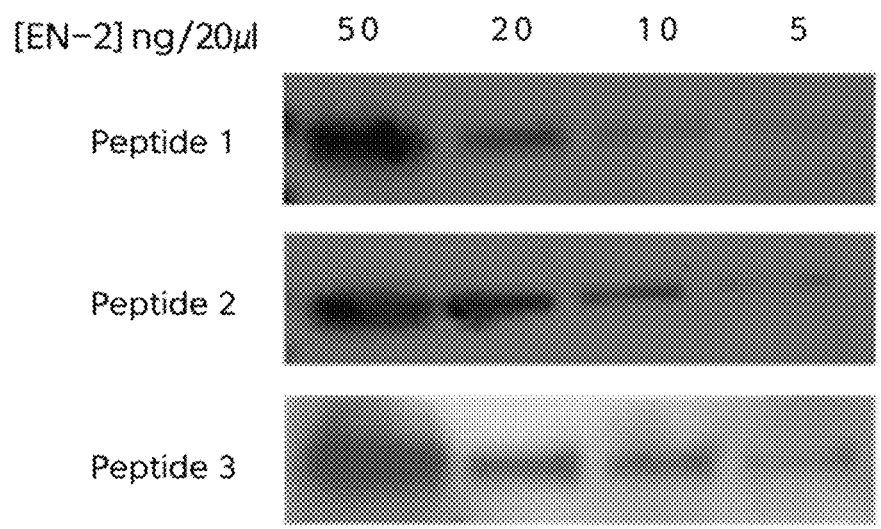
FIG. 6A and FIG. 6B show the quantitative results of western blotting assay of the antigen-detectable concentration by each antibody using recombinant EN2 protein.
Figure 6B:
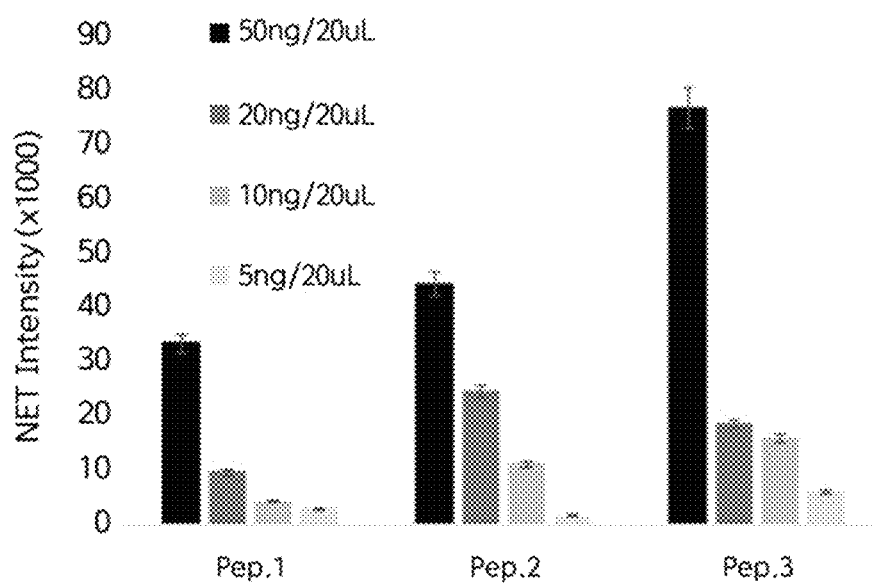

In lieu of the prostate cancer cell protein, the human EN2 recombinant protein prepared in Example 4 was diluted at concentrations from a maximum of 50 ng/20 µL (2.5 ng/µL) (60 nM) to a minimum of 5 ng/20 µL (0.25 ng/µL) (6 nM) and the sensitivity of the antibodies was measured under the same conditions as in Experimental Example 1. The results are shown in FIG. 6. FIG. 6a shows the band images obtained through western blotting, and FIG. 6b is a graph showing the numeric values of the results.

As shown in FIG. 6, all of the antibodies for three types of peptides exhibited EN2 protein detection sensitivity to a minimum of 5 ng/20 µL (0.25 ng/µL) (6 nM). This indicates that the antibodies prepared in the present invention have antibody sensitivity able to detect the EN2 protein concentration in actual patient urine (EN2 protein concentration range in the prostate cancer patient urine: 3.1 to 65.4 nM: Sci. Rep. 2013; 3: 2059).

Experimental Example 4. Evaluation of EN2 Protein Sensitivity in Urine

Considering that the sample from the subject to be diagnosed in the present invention is the urine of a prostate cancer patient, whether it was possible to detect EN2 protein in the secreted urine was tested. Particularly, recombinant EN2 protein was added to urine from a normal person at a concentration determined to be typical for urine of a prostate cancer patient, and was used immediately as a sample.

Figure 7A:
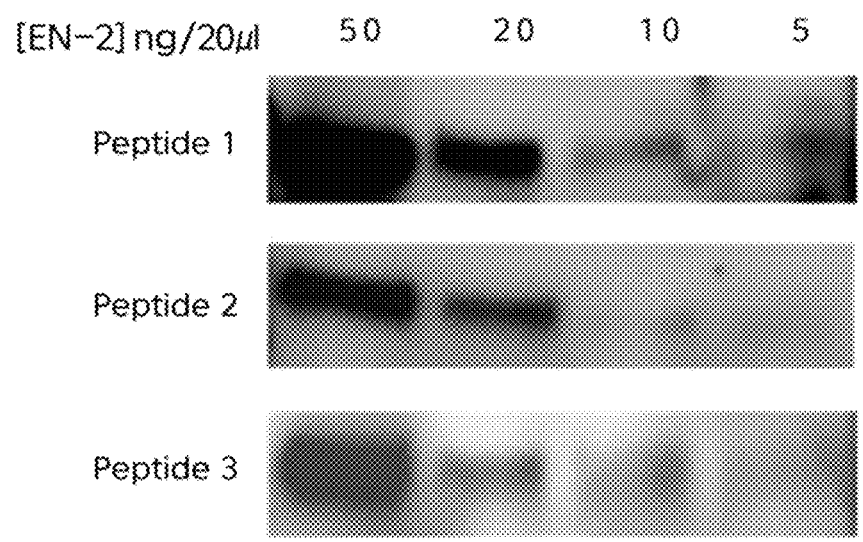
FIG. 7A and FIG. 7B show the results of western blotting assay of the antigen-detectable concentration in the urine using recombinant EN2 protein.
Figure 7B:
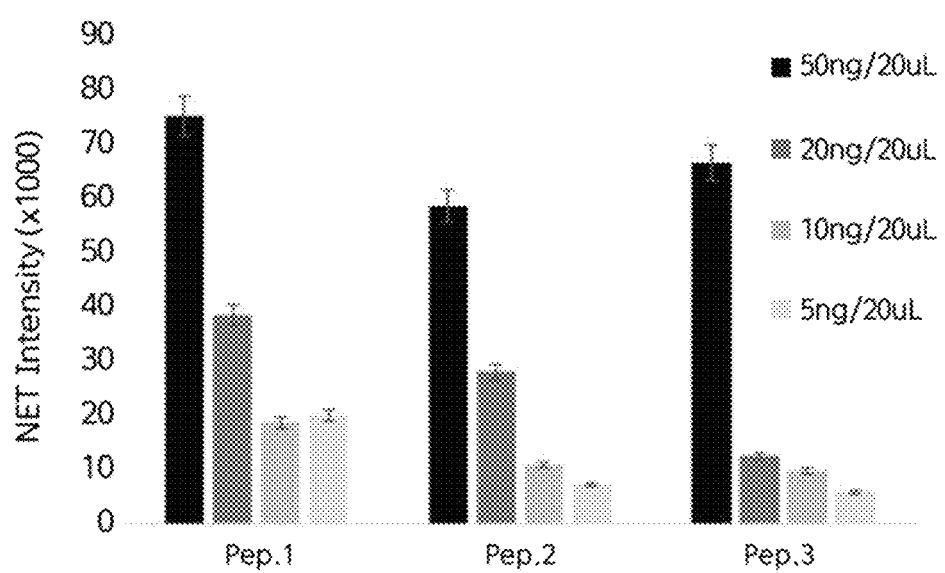

Here, the concentration of the recombinant protein and the entire experimental procedure were the same as in Experimental Example 3. The results are shown in FIG. 7. FIG. 7a shows the band images obtained through western blotting, and FIG. 7b is a graph showing the numeric values of the results.

As shown in FIG. 7, despite the effects of organic/ inorganic materials contained in the urine, all of the respective antibodies recognizing the three peptides were able to detect the antigen up to a minimum concentration of 0.25 ng/µL (6 nM).

Experimental Example 5. Evaluation of Detection Ability Through Immunofluorescence Staining Testing in Cell Line (LNCap)

Figure 8A:
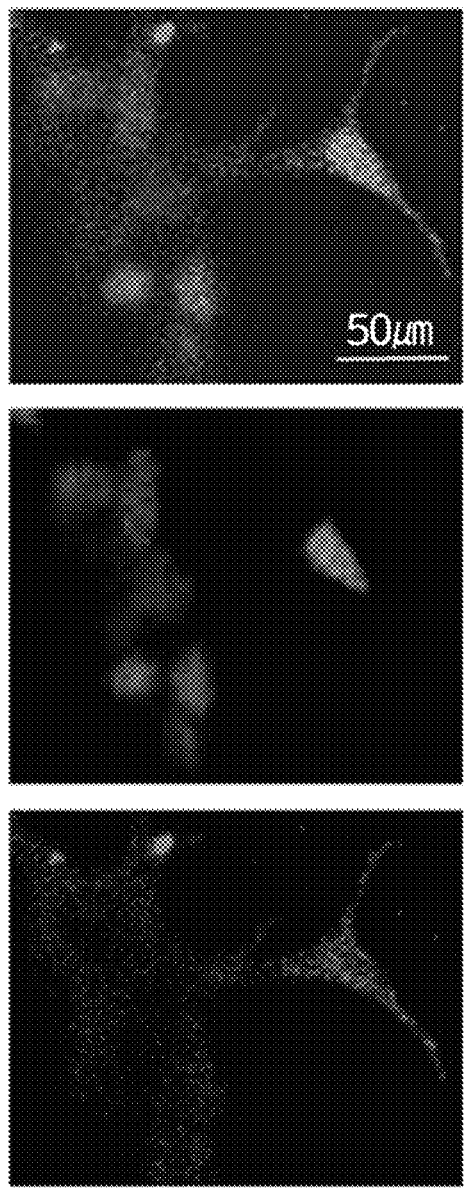
Figure 8B:
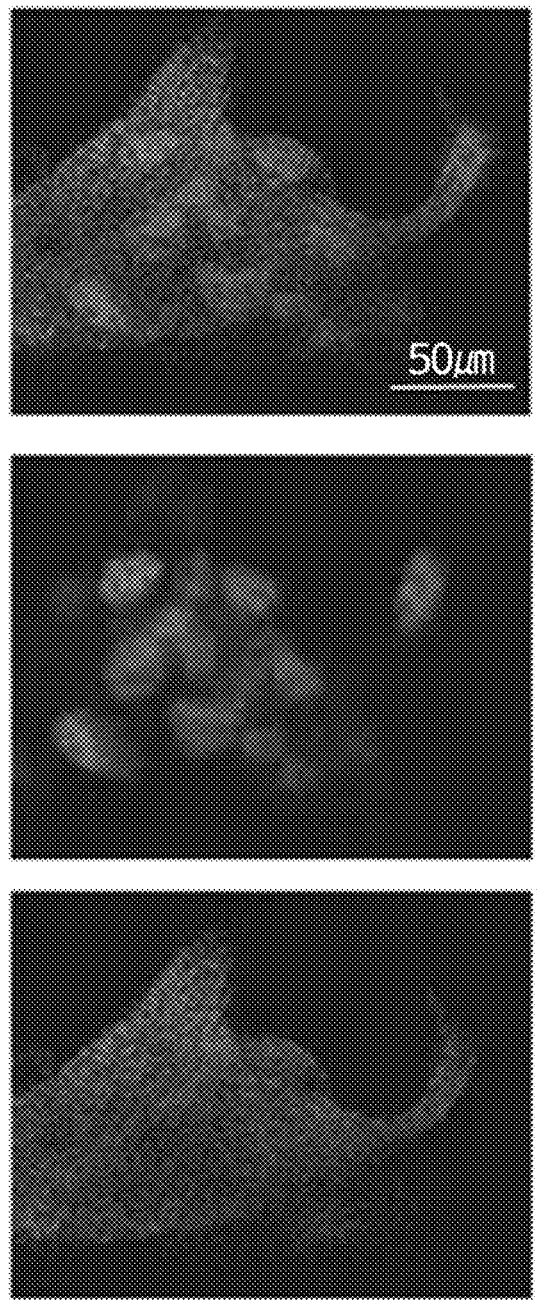

The intracellular EN2 protein of the prostate cancer cell line (LNCap) was detected based on antigen-antibody specificity. As the primary antibody, the three types of antibodies prepared in Example 3 were used, and as the secondary antibody, anti-rat IgG/FITC was used, and the binding capacity to the antigen distributed in the cytoplasm was analyzed through confocal laser microscopy. The fluorescence staining images thereof are shown in FIG. 8. FIG. 8a shows the results of Peptide 1, FIG. 8b shows the results of Peptide 2, and FIG. 8c shows the results of Peptide 3.

As shown in FIG. 8, all of the three types of antibodies can be confirmed to bind to the EN2 protein distributed in the cells, whereby the antibody of the present invention can be easily used, even for antigen detection under non-denaturation conditions.

Experimental Example 6. Evaluation of Sensitivity Using Recombinant EN2 Protein ($K_d$: Dissociation Constant)

The recombinant EN2 protein was attached to a 96-well plate at 4° C. overnight, and blocking was carried out at 37° C. using a TBST solution containing 2% skim milk. Here, the experiment was progressed under the condition that the recombinant EN2 protein was fixed at 250 ng/well and the antibody was subjected to serial dilution (FIG. 9), and the experiment was progressed under the condition that the antibody was fixed and the antigen was diluted at 0.5 to 50 ng/mL (FIG. 10).

Thereafter, each well was treated with the primary antibody, and with, as the secondary antibody, HRP-conjugated anti-rat IgG diluted at 1/10000. After the reaction, a color development reaction was progressed using a TMB (3,3',5,5'-tetramethylbenzidine) solution and terminated using a 1 N sulfuric acid.

The resultant values were quantified using an ELISA reader and the Kd value was calculated using the association kinetics method of the Prism program. The results are shown in FIG. 9, and the EN2 content detected by each antibody is shown in FIG. 10.

Figure 9A:
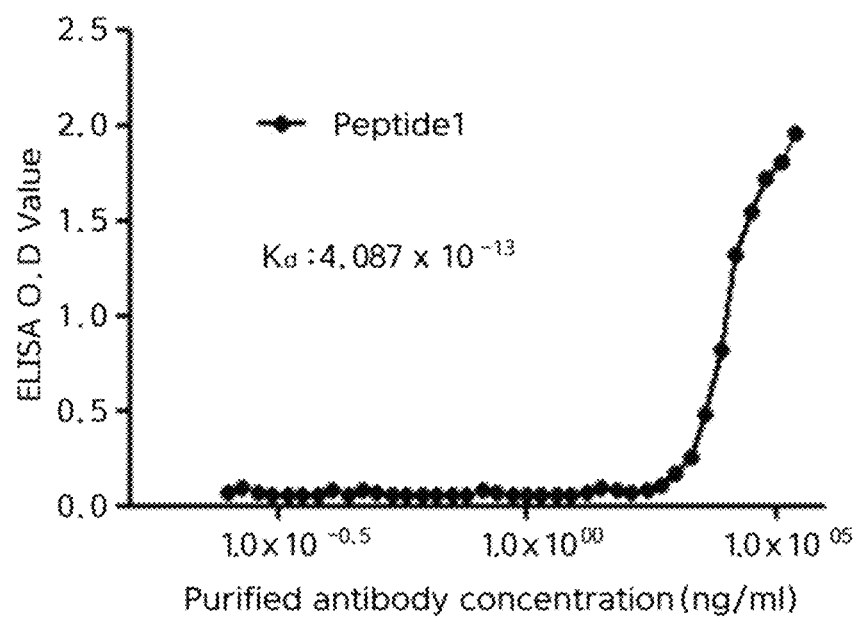
FIG. 9A, FIG. 9B, and FIG. 9C show the results of ELISA of the dissociation constant for the binding capacity of the purified antibody and the antigen using recombinant EN2 protein.
Figure 9B:
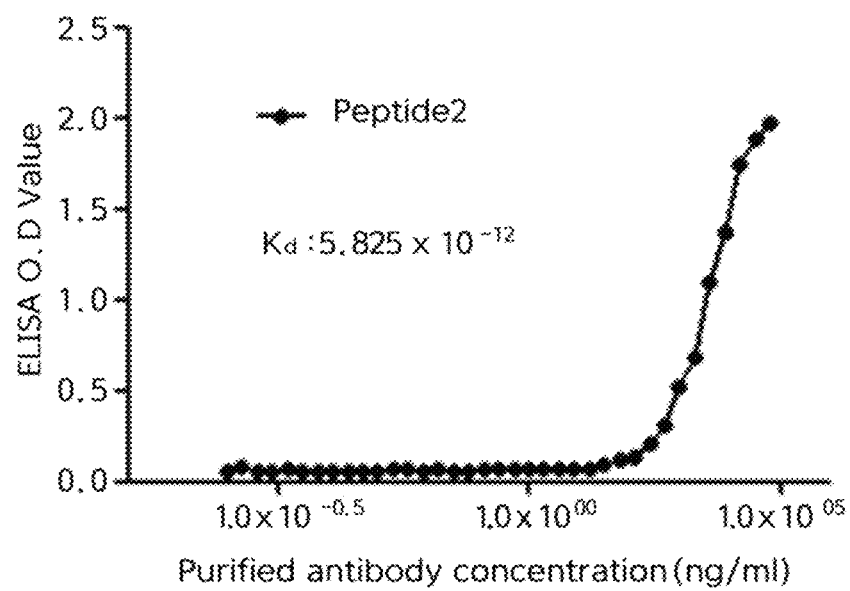
Figure 9C:
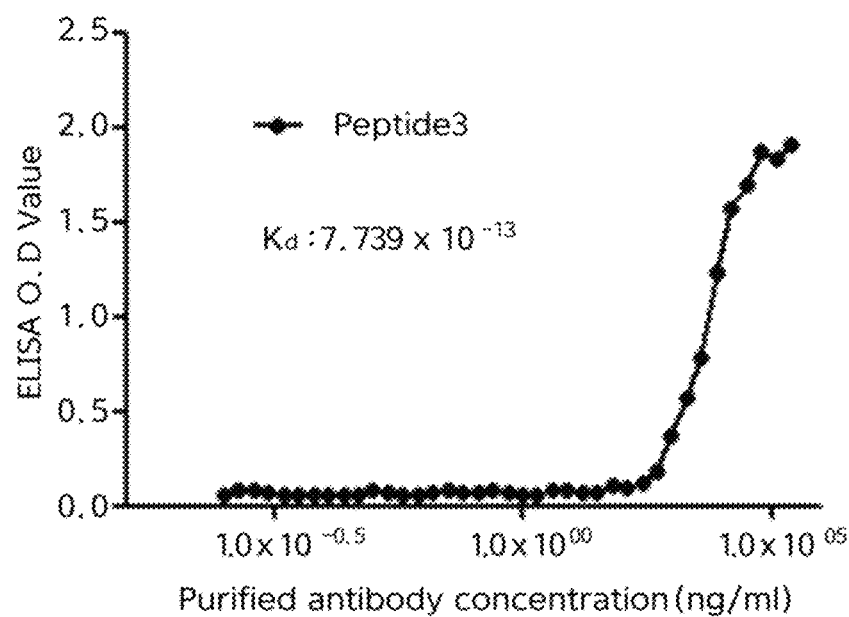
Figure 10:
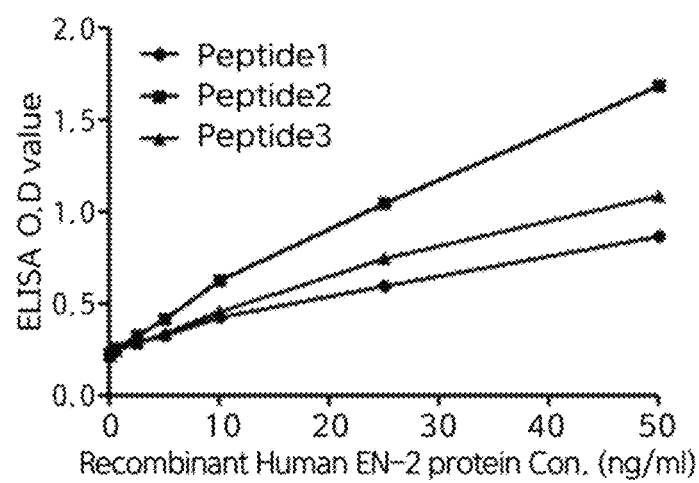
FIG. 10 shows the results of ELISA measurement of affinity of the purified antibody for the antigen using recombinant EN2 protein.
Figure 11:
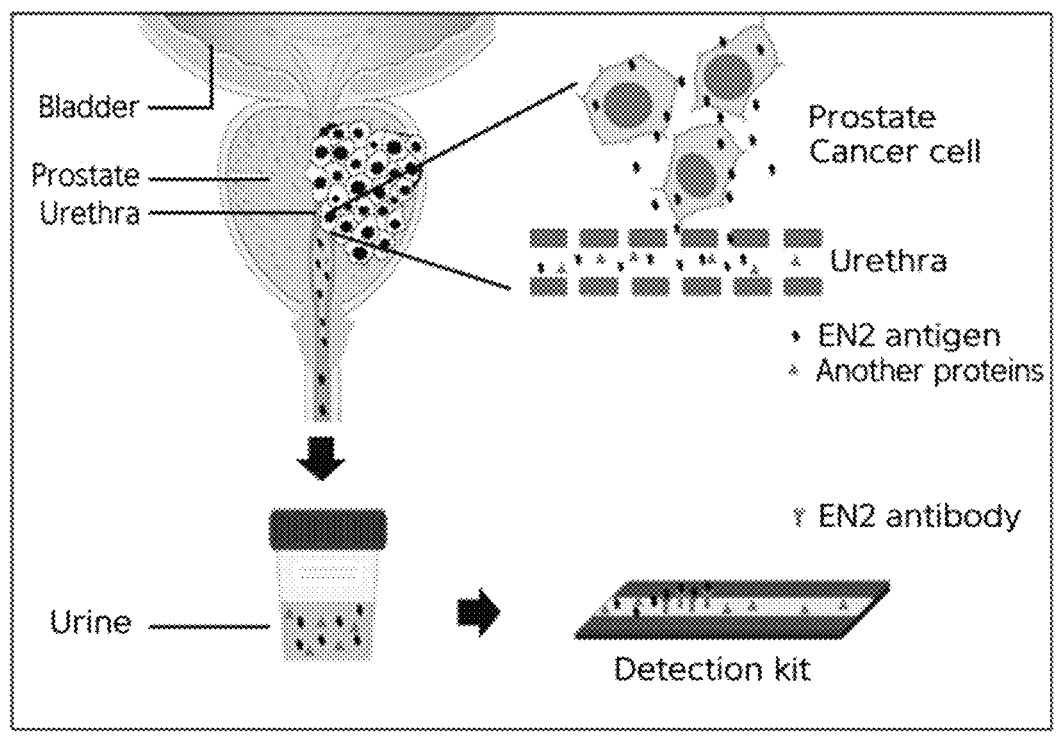
FIG. 11 schematically shows a process of evaluating the presence and expression level of the EN2 protein, which is a biomarker for the diagnosis of prostate cancer in the urine, using an antibody composition of the present invention.

As shown in FIG. 9, the dissociation constant Kd is the amount of antigen required to occupy ½ of the antibody-binding site, and an antibody having high affinity for an antigen has a small dissociation constant. The Kd values of the antibodies are as follows: Peptide 1: $4.087 \times 10^{-13}$, Peptide 2: $5.825 \times 10^{-12}$, and Peptide 3: $7.739 \times 10^{-13}$. Also, the antibody for Peptide 3 showed the highest value, and compared to a normal natural antibody having a Kd value of $10^{-7}$ to $10^{-10}$, the developed antibody had a Kd value of $10^{-12}$ to $10^{-13}$ and thus manifested a high titer, whereby the antibody (prepared in Example 3 according to the present invention) having high binding capacity to the recombinant EN2 protein antigen was confirmed to be prepared.

With reference to FIG. 10 and Table 2 below, all of three antibodies were able to detect EN2 antigen up to a minimum concentration of 0.5 ng/mL through ELISA.

TABLE 2

| | ELISA O.D. value (EN2 protein) | | | | | | |
|---|---|---|---|---|---|---|---|
| | 0 ng/mL | 0.5 ng/mL | 2.5 ng/mL | 5 ng/mL | 10 ng/mL | 25 ng/mL | 50 ng/mL |
| Pep1 | 0.22250 | 0.25425 | 0.28450 | 0.32425 | 0.42175 | 0.59700 | 0.86575 |
| Pep2 | 0.22575 | 0.25775 | 0.32350 | 0.41600 | 0.62900 | 1.04650 | 1.68600 |
| Pep3 | 0.21350 | 0.24575 | 0.28825 | 0.33400 | 0.46075 | 0.74275 | 1.09133 |

Therefore, these results show that the antibody of the present invention is deemed to be an excellent antibody because it can be utilized not only in a qualitative test to determine the presence of cancer, but also a quantitative test to evaluate the progression of cancer by quantifying the correlation between EN2 detection in the urine and cancer progression.

Figure 12:
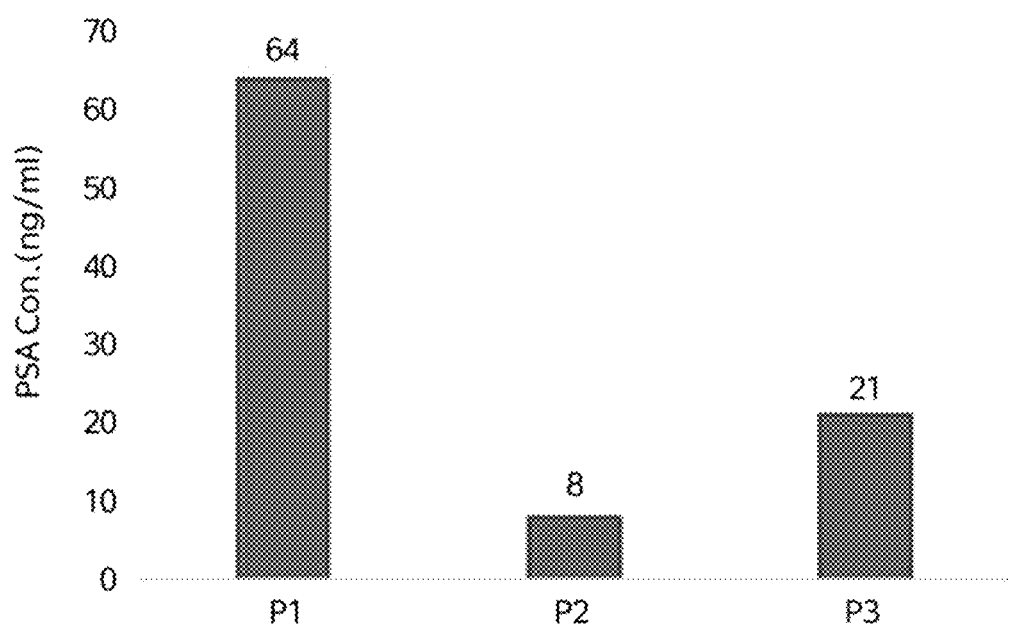
FIG. 12 shows the quantitative analysis results of PSA (prostate-specific antigen) through ELISA from the blood in three prostate cancer patients.
Figure 13:
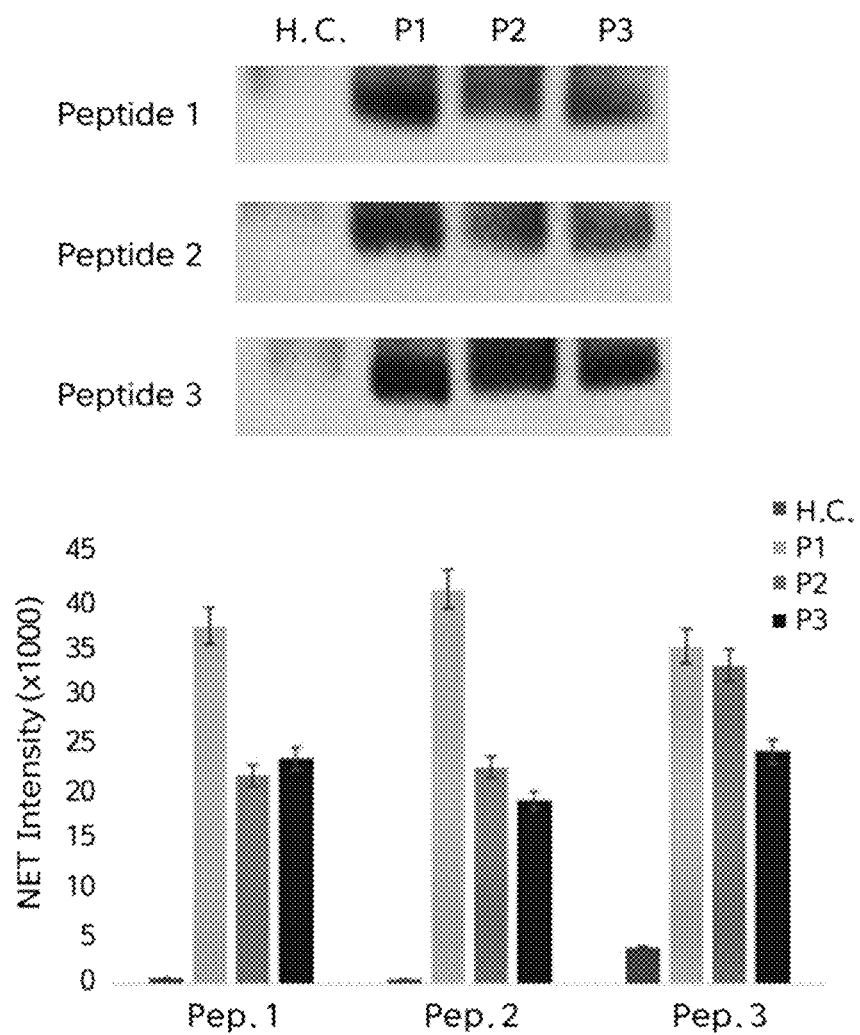
FIG. 13 shows the results of western blotting assay of the presence and expression level of the EN2 protein, which is a biomarker for the diagnosis of prostate cancer in the urine, using the antibody composition of the present invention.

Experimental Example 7. Evaluation of Efficacy in Prostate Cancer Patient Urine Sample In order to evaluate EN-2 detection ability in the prostate patient urine sample for use in actual tests, three prostate cancer patient samples (P1, P2, P3) were centrifuged at 10000 g for 10 min and the supernatant was isolated and subjected to western blotting. 15 μL of the urine sample was mixed with 5 μL of a 4× sample buffer and boiled at 100° C. for 5 min, and western blotting was carried out. Here, the concentration of the antibody used was 3.3 nM, and as a negative control (H.C.), urine from healthy males was used. The results are shown in FIG. 13. The PSA expression results of prostate cancer patients, obtained through ELISA as in Experimental Example 6, are shown in FIG. 12.

With reference to FIG. 13, all of the three types of antibodies of the present invention can be concluded to exhibit high EN-2 detection ability in actual patient samples.

What is claimed is:

1. A polyclonal antibody composition specifically recognizing a peptide consisting of an amino acid sequence of SEQ ID NO: 2 (CTRYSDRPSSGPRSRKPKKKNPNKEDKRPR),
    wherein the peptide is an immunogenic fragment of an EN2 (engrailed-2) protein.

2. A diagnostic agent for diagnosing prostate cancer, containing the polyclonal antibody composition of claim 1.

* * * * *

SEQUENCE LISTING

<160> NUMBER OF SEQ ID NOS: 5

<210> SEQ ID NO 1
<211> LENGTH: 30
<212> TYPE: PRT
<213> ORGANISM: Homo sapiens

<400> SEQUENCE: 1

Pro Gly Asp Gly Glu Gly Gly Ser Lys Thr Leu Ser Leu His Gly Gly
1               5                   10                  15

Ala Lys Lys Gly Gly Asp Pro Gly Gly Pro Leu Asp Gly Ser
            20                  25                  30

<210> SEQ ID NO 2
<211> LENGTH: 30
<212> TYPE: PRT
<213> ORGANISM: Homo sapiens

<400> SEQUENCE: 2

Cys Thr Arg Tyr Ser Asp Arg Pro Ser Ser Gly Pro Arg Ser Arg Lys
1               5                   10                  15

Pro Lys Lys Lys Asn Pro Asn Lys Glu Asp Lys Arg Pro Arg
            20                  25                  30

<210> SEQ ID NO 3
<211> LENGTH: 29
<212> TYPE: PRT
<213> ORGANISM: Homo sapiens

<400> SEQUENCE: 3

Pro Arg Ser Arg Lys Pro Lys Lys Asn Pro Asn Lys Glu Asp Lys
1               5                   10                  15

Arg Pro Arg Thr Ala Phe Thr Ala Glu Gln Leu Gln Arg
            20                  25

<210> SEQ ID NO 4
<211> LENGTH: 29
<212> TYPE: PRT
<213> ORGANISM: Homo sapiens

<400> SEQUENCE: 4

Glu Asp Lys Arg Pro Arg Thr Ala Phe Thr Ala Glu Gln Leu Gln Arg
1               5                   10                  15

Leu Lys Ala Glu Phe Gln Thr Asn Arg Tyr Leu Thr Glu
            20                  25

<210> SEQ ID NO 5
<211> LENGTH: 125
<212> TYPE: PRT
<213> ORGANISM: Homo sapiens

<400> SEQUENCE: 5

Gly Thr Cys Cys Ala Gly Ala Gly Gly Arg Gly Gly Gly Ala Gly
1               5                   10                  15

Gly Glu Gly Gly Ala Ser Gly Ala Glu Gly Gly Gly Ala Gly Gly
            20                  25                  30

Ser Glu Gln Leu Leu Gly Ser Gly Ser Arg Glu Pro Arg Gln Asn Pro
        35                  40                  45

Pro Cys Ala Pro Gly Ala Gly Gly Pro Leu Pro Ala Ala Gly Ser Asp
    50                  55                  60

Ser Pro Gly Asp Gly Glu Gly Gly Ser Lys Thr Leu Ser Leu His Gly
65                  70                  75                  80

Gly Ala Lys Lys Gly Gly Asp Pro Gly Gly Pro Leu Asp Gly Ser Leu
                85                  90                  95

-continued

```
Lys Ala Arg Gly Leu Gly Gly Asp Leu Ser Val Ser Ser Asp Ser
            100                 105                 110

Asp Ser Ser Gln Ala Gly Ala Asn Leu Gly Ala Gln Pro
        115                 120                 125
```